United States Patent [19]

Martinez

[11] Patent Number: 5,189,920
[45] Date of Patent: Mar. 2, 1993

[54] CORNER STABILITY TESTING APPARATUS

[75] Inventor: Rosendo Martinez, St. Louis, Mo.

[73] Assignee: Electronics & Space Corp., St. Louis, Mo.

[21] Appl. No.: 672,833

[22] Filed: Mar. 21, 1991

[51] Int. Cl.$^5$ ................... G01M 17/00; G01N 19/02
[52] U.S. Cl. .......................................... 73/865.3; 73/9;
 73/866.4; 73/865.9
[58] Field of Search ................ 73/866.4, 865.9, 865.3,
 73/865.6, 9, 10; 434/67, 305

[56] References Cited

U.S. PATENT DOCUMENTS

| | | | |
|---|---|---|---|
| 3,654,728 | 4/1972 | Beny et al. | 73/9 X |
| 4,073,188 | 2/1978 | Slezinger et al. | 73/147 |
| 4,700,798 | 10/1987 | Johansson et al. | 434/67 X |
| 4,753,173 | 6/1988 | James | 104/45 |
| 4,941,794 | 7/1990 | Hara et al. | 414/341 |
| 4,971,314 | 11/1990 | Barber | 104/69 X |

FOREIGN PATENT DOCUMENTS

| | | | |
|---|---|---|---|
| 2387063 | 12/1978 | France | 73/9 |
| 10627 | 1/1983 | Japan . | |
| 287239 | 11/1990 | Japan | 73/9 |
| 888018 | 12/1981 | U.S.S.R. | 73/9 |

OTHER PUBLICATIONS

"Auto S/mpers down runways to sample friction of wet or icy landing surfaces", Electronics (USA) vol. 51, No. 8, Apr. 13, 1978 pp. 70, 72; in 73/9.
Mechanics of Vehicles Chapter 4, "Stabilzation Curve" by Jeruslav J. Taburek; published by May 1990; 5 pp.
"Vehicle Cornering Stability and CG Limits"; SAWE paper No. 1930 by Rosendo Martinez presented at 49th Annual Conference of Society of Allied Weight Engineers, Inc. in Mesa, Ariz. 21-23 May 1990 pp. 1–40.

Primary Examiner—Tom Noland
Attorney, Agent, or Firm—Polster, Lieder, Woodruff & Lucchesi

[57] ABSTRACT

Apparatus (10) for testing the cornering stability of a vehicle (12) to determine when the vehicle begins to slide or tip over when rounding a corner. A movable platform (32) is capable of supporting the weight of a vehicle, and the vehicle is positioned on one end of the platform. A counterweight (42) is positioned at the opposite end of the platform. The platform is rotatable through a range of speeds to simulate vehicle movement in a circular path such as when the vehicle is rounding a corner. Sensors are attached to wheels (T3, T4) of the vehicle to detect a sliding movement of the vehicle relative to the platform. A lifting movement which occurs when the vehicle begins to tip over, is also detectable. A method of determining a vehicle's center of gravity which will provide stability is also disclosed.

19 Claims, 7 Drawing Sheets

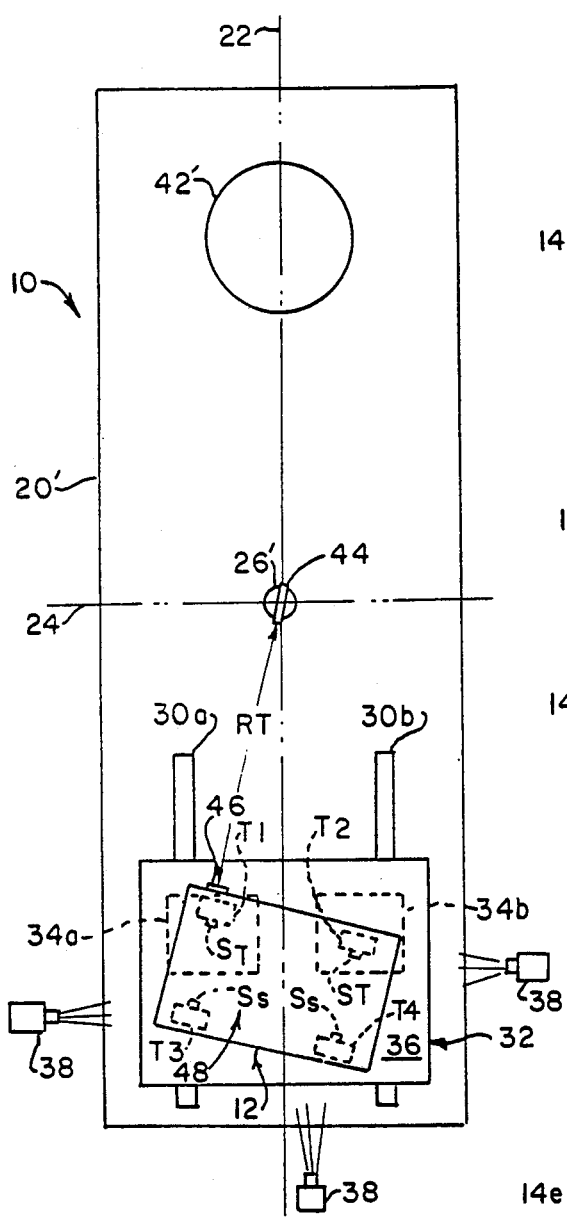
FIG. 6.
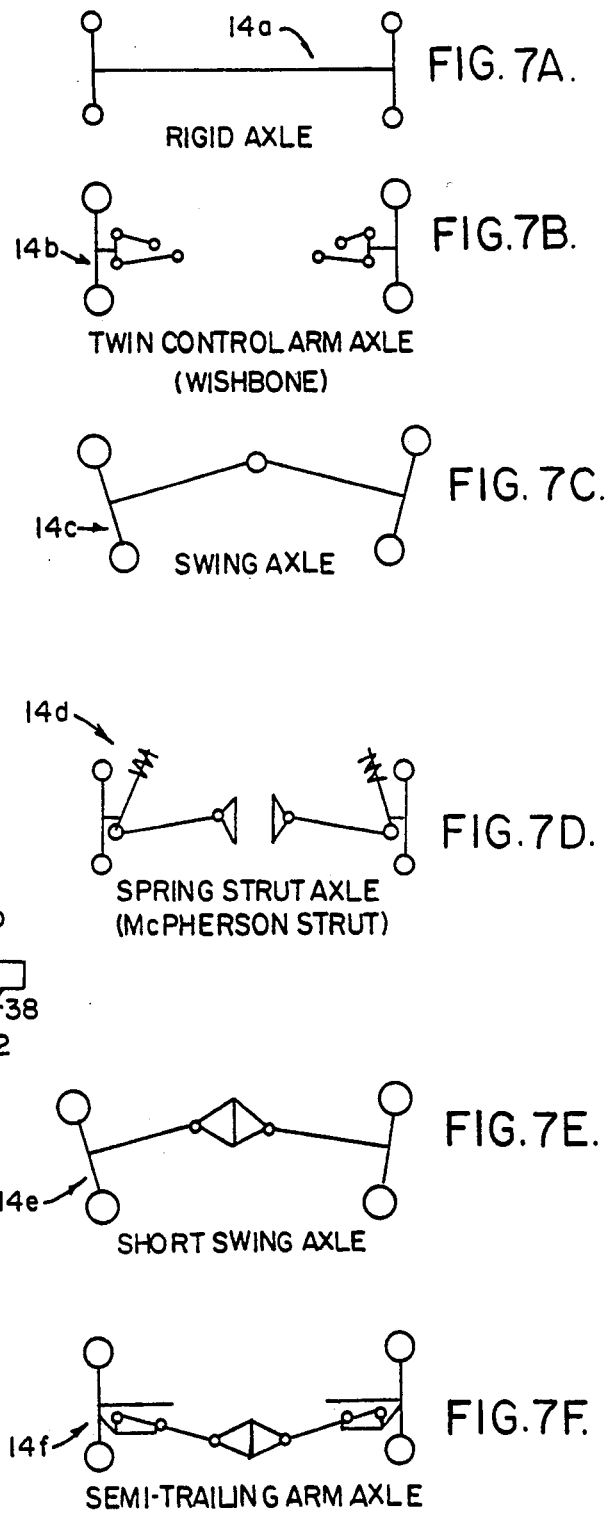

CORNER STABILITY TESTING APPARATUS

BACKGROUND OF THE INVENTION

This invention relates to automobile safety and, more particularly, to apparatus for testing the cornering capability of automotive vehicles to refine vehicle design and develop suspension systems which will enhance the cornering capabilities of the vehicle and prevent rollover accidents.

One cause of injuries and deaths in automotive vehicle accidents is rollover. Rollover typically occurs when the vehicle is traveling in a circular rather than a straight direction (as when the vehicle is rounding a curve). If, when traveling on this circular path, the centrifugal, inertial force becomes so large the moment on the outer wheels of the vehicle exceeds the restoring moment produced by the vehicle's weight around these same wheels, the vehicle may turn over. There are a number of factors which influence whether or not rollover occurs. See, for example STABILITY ON A CURVE by Jaroslav J. Taberek, Mechanics of Vehicles, Chapter 4. Among these are whether the vehicle has a high or low center of gravity (cg), whether the wheel tread is wide or narrow, the type of road surface (concrete, asphalt, dirt, ice), the coefficient of friction between the vehicle's tires and the road, the vehicle's suspension system, etc. Various of these factors are treated in my paper VEHICLE CORNERING STABILITY AND CG LIMITS which was presented to the Society of Allied Weight Engineers, Inc. (SAWE) at their annual conference held May 21-23, 1990.

The determination of a vehicle's cornering stability is important because of the occupants, safety. By stability is meant that the vehicle slides on a turn before it turns over. If a vehicle is sliding, the driver has the opportunity to correct the maneuver. If the vehicle tips over before it starts to slide, it is almost impossible for the driver to do anything to prevent a rollover. Consequently, if factors can be determined which promote sliding rather than tipping and these can be incorporated into the vehicle's design, the chances of rollover accidents may be greatly lessened.

SUMMARY OF THE INVENTION

Among the several objects of the present invention may be noted the provision of apparatus for testing the cornering stability of a vehicle; the provision of such apparatus for testing the vehicle's cornering stability for a variety of different road surfaces conditions; the provision of such apparatus for testing different vehicle suspension systems, tires, weight distribution, etc.; the provision of such apparatus to determine whether a vehicle begins to slide before tipping or vice versa; the provision of such apparatus produce data useful in designing various types of vehicles; and, the provision of a method for determining the center of gravity of a vehicle which will provide it stability under a wide variety of road conditions.

In accordance with the invention, generally stated, apparatus of the present invention is for testing the cornering stability of a vehicle to determine when the vehicle begins to slide or tip over when rounding a corner. A movable platform is capable of supporting the weight of a vehicle, and the vehicle is positioned on one end of the platform. A counterweight is positioned at the opposite end of the platform. The platform is rotatable through a range of speeds to simulate vehicle movement in a circular path such as when the vehicle is rounding a corner. Sensors are attached to each wheel of the vehicle to detect movement of the vehicle relative to the platform. This movement is either a lifting movement which occurs when the vehicle begins to tip over, or a sliding movement such as occurs when the vehicle begins to skid. A method of determining a vehicle's center of gravity which will provide stability under a variety of road conditions is also disclosed. Other objects and features will be in part apparent and in part pointed out hereinafter.

BRIEF DESCRIPTION OF THE DRAWINGS

FIG. 6 is a top plan view of the apparatus of FIG. 5;

FIGS. 7a-7f are diagrams of various types of vehicle suspension systems which can be tested using the apparatus.

FIGS. 8-13 are schematic representations of a wishbone suspension system, wherein FIG. 8 is a representation of a forward wishbone suspension leaning in a turn;

FIG. 9 is a representation of the rear wishbone suspension leaning in the turn;

FIG. 10 is a representation of the forward wishbone suspension with one tire lifting off the ground and at the moment before the other axle's tire lifts clear of the ground;

FIG. 11 represents the geometric relation of a vehicle's forward suspension;

FIG. 12 represents the geometrical relationship between the forward and rear suspensions at a station corresponding to the vehicle's center of gravity;

FIG. 13 represents the geometrical relationship at the vehicle's rear suspension;

Corresponding reference characters indicate corresponding parts throughout the drawings

DESCRIPTION OF PREFERRED EMBODIMENTS

Figure 1A:
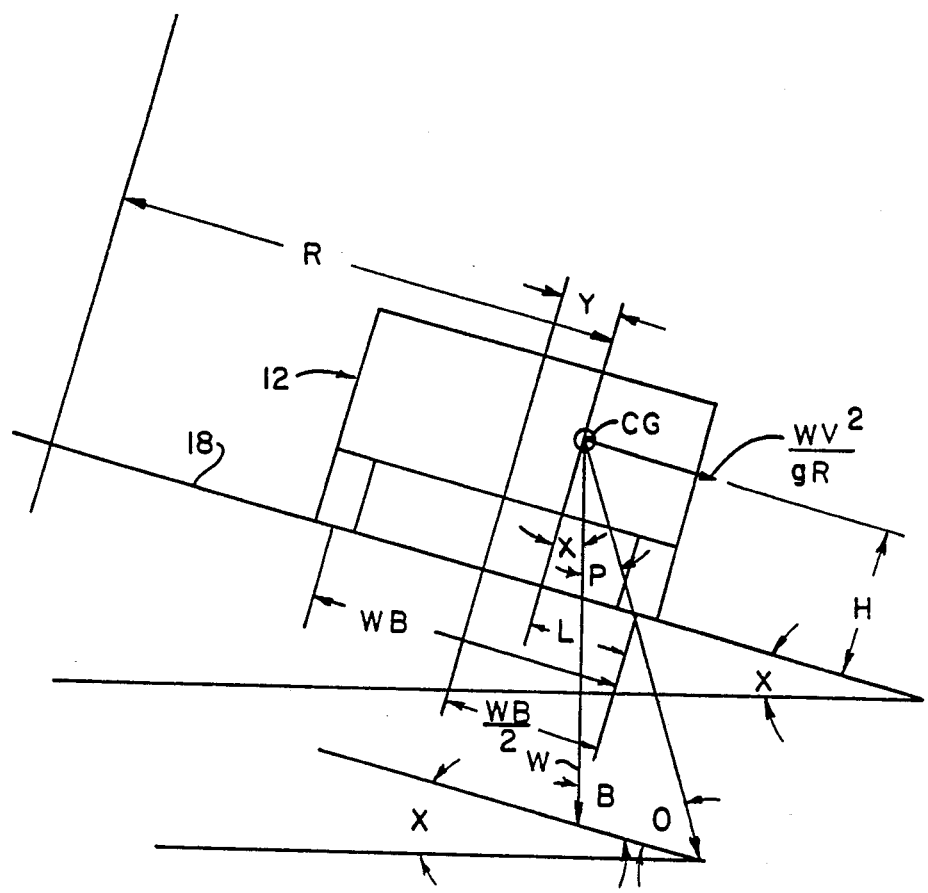
FIGS. 1a-1c are diagrams including a free body diagram illustrating a first type of vehicle cornering condition for which the apparatus of the present condition can test.
Figures 2A, 2C:
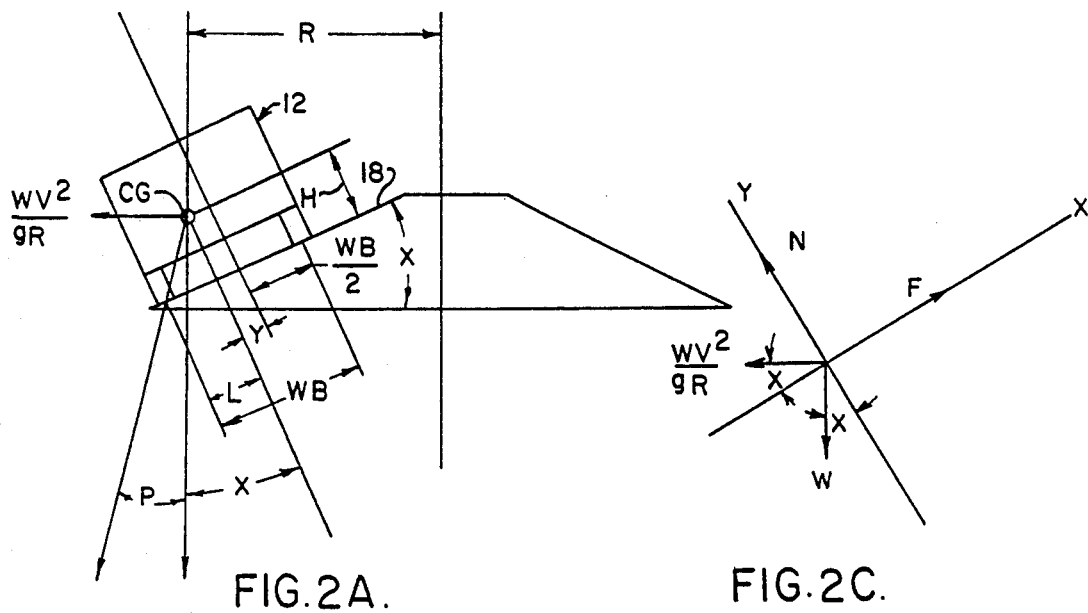
FIGS. 2a-2c are diagrams including a free body diagram illustrating a second type of vehicle cornering condition for which the apparatus of the present condition can test.
Figure 2B:
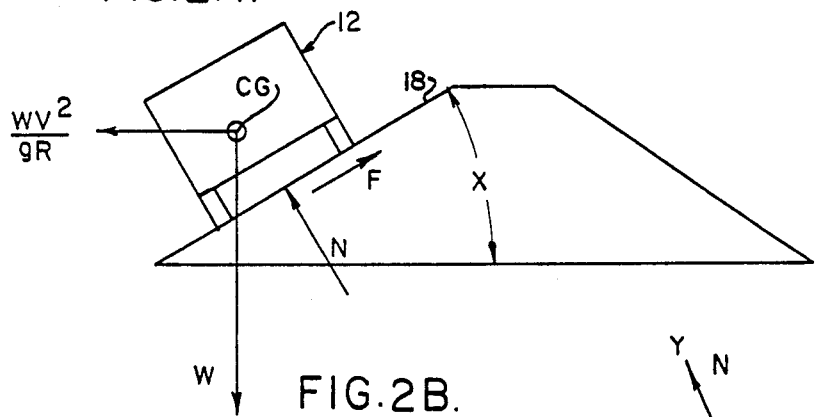
Figures 3A, 3C:
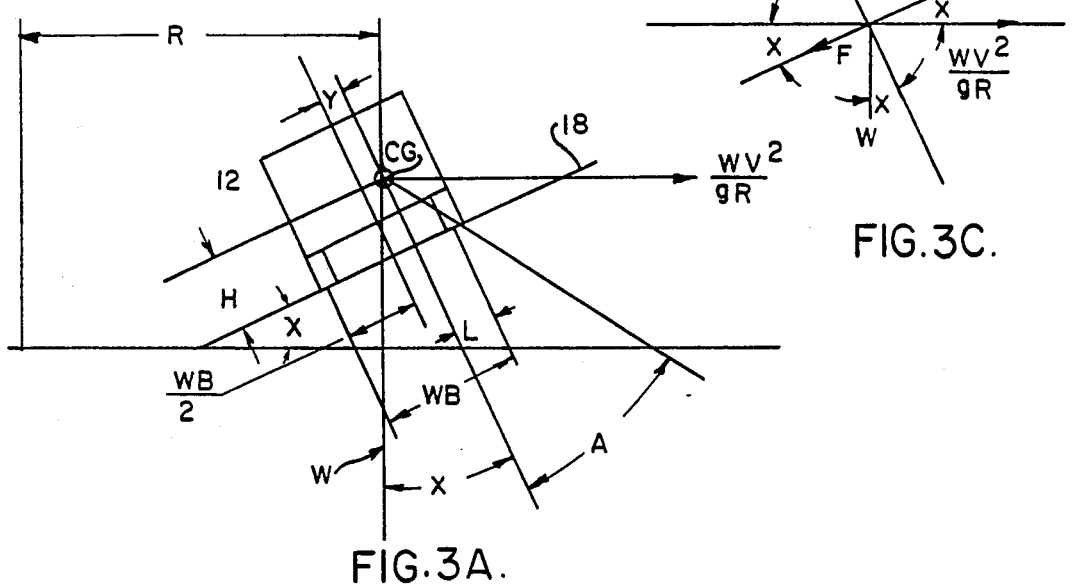
FIGS. 3a-3c are diagrams including a free body diagram illustrating a third type of vehicle cornering condition for which the apparatus of the present condition can test.
Figure 3B:
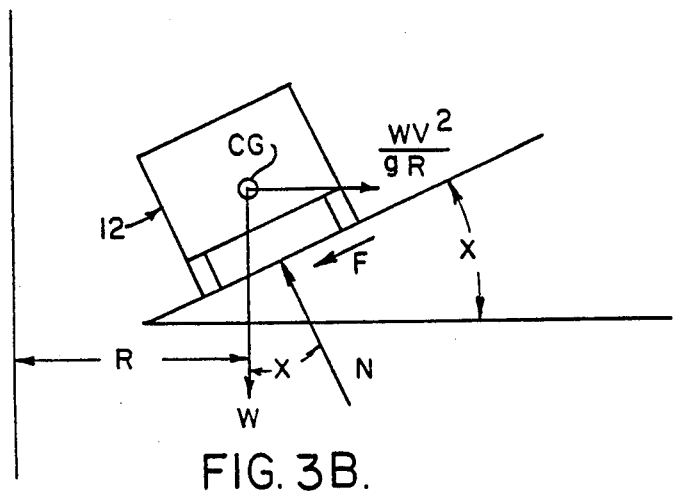
Figure 4A:
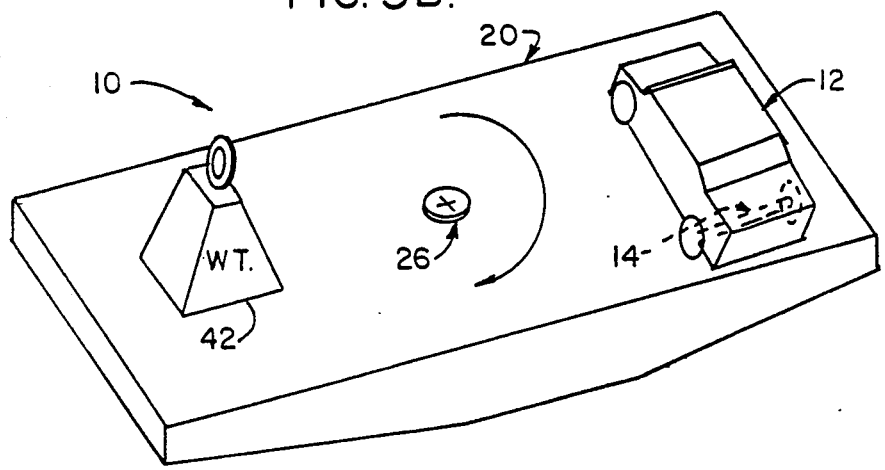
FIGS. 4a and 4b are respective top plan views of two embodiments of a testing apparatus for testing the design of a vehicle and its suspension system.
Figure 4B:
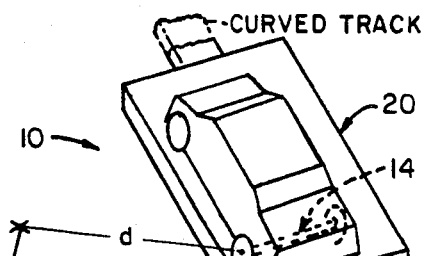

Referring to the drawings, apparatus 10 (see FIG. 4a) of the present invention is for testing an automotive vehicle 12 to determine if the vehicle's suspension system 14 (see FIGS. 7A-7F) will prevent the vehicle from tipping over when turning through a corner. A vehicle is considered cornering stable when it slides on a turn before tipping over. It will be understood that while the vehicle's shown in the accompanying drawings are four wheeled vehicles, the vehicle's with which apparatus 10 can be used may include three-wheeled vehicles and tracked vehicles. In addition, the various formulas which are included in this specification, are applicable to any of the above types of vehicles. Apparatus 10 is useful in testing whether the vehicle design and the suspension system used with the vehicle will indeed allow it to slide before tipping in various turn situations. For this purpose, vehicle 12 is placed upon one end of a rotatable platform 20 and a counterweight 42 is positioned on the opposite end of the platform. During a test, the platform is rotated about an axis corresponding to the vertical centerline of a drive shaft 26 to determine if the vehicle slides or tips. As is described hereinafter, the platform is rotatable at various speeds to ascertain the dynamic characteristics of the vehicle's suspension system together with other vehicle design features. With respect to FIG. 4b, it will be appreciated that platform 20 may be installed on and movable over a curved track 21. In addition, the platform may be tiltable with respect to the track to simulate the angle of the turn. Lastly, the distance d from the axis 26 to the platform represents the radius of the curve. In the design of a vehicle 12, factors which are important for cornering stability include the maximum velocity at which the vehicle can be driven in a turn before tipping over (assuming an infinite coefficient of friction between the road and the tires) and the maximum velocity at which it can be driven before it slides. Three different turning situations for vehicle 12 are shown in FIGS. 1-3. These are:

turning uphill on an incline (FIGS. 1a-1c);
turning around the side of a hill (FIGS. 2a-2c); and,
turning on a banked road (FIGS. 3a-3c).

The following analysis is for the turning situation shown in FIG. 1a. For the analysis, the following symbols represent the following characteristics:

CG = vehicle's 12 center of gravity
V = vehicle's velocity (ft/sec), (V*0.6818 = velocity in mph)
R = radius of turn (ft)
g = acceleration due to gravity (32.1725 ft/sec)
H = vertical distance from vehicle's center of gravity to the ground (in)
W = vehicle's weight (lb) (
Y = horizontal lateral distance between mid-point of vehicle and its center of gravity (in)
WB = horizontal lateral distance between the center of the wheels (in)
L = horizontal lateral distance between the vehicle's center of gravity and the center of the wheels on the downhill side of the vehicle (in)
X = angle of incline of the roadway 18 to the horizontal (deg)

In addition, the following relationships exist:

$B = X + 90$ degrees
$O = 180$ degrees $- B - X$
$= 180 - (X + 90) - P$
$= 90 - X - P$
$P = 180$ degrees $- B - O$ Given the foregoing, the following dynamic relationship exists $$W/\sin O = (WV^2/GR)/\sin P$$

Solving for $V^2$, $$V^2 = G*R*\sin P/\sin O$$

From the above relationships, it can be shown that:

$$\text{Tan }(X+P) = L/H, \text{ or } (X+P) = \text{Tan}^{-1}(L/H)$$

Further, $$P = (X+P) = X$$

Substituting, $$V^2 = G*R*\sin[(X+P) - X]/\sin O,$$
$$= G*R*\sin[\text{Tan}^{-1}(L/H) - X]/\sin(90 - X - P)$$
$$= G*R*\sin[\text{Tan}^{-1}(L/H) - X]/\sin[90 - X - [(X+P) - X]]$$
$$= G*R*\sin[\text{Tan}^{-1}(L/H) - X]/\sin[90 - (X+P)]$$

So that, $$V = [G*R*\sin[\text{Tan}^{-1}(L/H) - X]/\sin[90 - \text{Tan}^{-1}(L/H)]]^{\frac{1}{2}}$$

or $$V1_t = [G*R*\sin]\text{Tan}^{-1}(L/H) - X]/\cos[\text{Tan}^{-1}(L/H)]]^{\frac{1}{2}}$$

Without going through the derivation, it will be understood that with respect to the situation shown in FIG. 2a, it can be mathematically shown that $$V2_t = [G*R*[((L/H) - \text{Tan }X)/(1 + (L/H)*\text{Tan }X)]]^{\frac{1}{2}}$$

and that with respect to the situation shown in FIG. 3a, $$V3_t = [G*R*[((H*\text{Tan }X) + L)/(H - (L*\text{Tan }X))]]^{\frac{1}{2}}$$

where, with respect to the angle A shown in FIG. 3a, $$\text{Tan }(X+A) = V^2/G*R$$

Figure 1B:
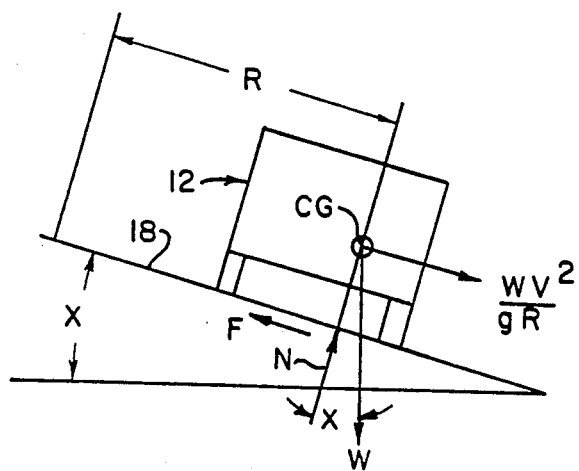
Figure 1C:
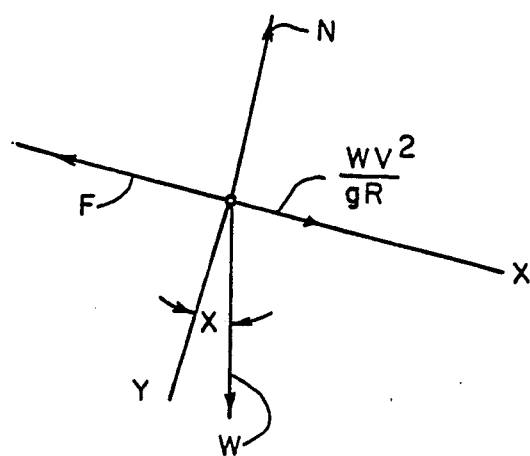

The respective equations for $V1_t$, $V2_t$, and $V3_t$ all represent the maximum velocity at which vehicle 12 can be driven in the various cornering situations without tipping over. Since apparatus 10 is also used to determine the maximum velocity at which the vehicle can be driven before it begins to slide in each of these situations, equations for these values are also of interest. Referring to FIGS. 1b and 1c, where FIG. 1c is a free body diagram for the situation shown in FIG. 1b, N = the force normal into the vehicle, and
u = the coefficient of friction (dimensionless).

Summing the forces along the x-axis in FIG. 1c,
$$O_x = (W*V^2)/(G*R) - F + W*\sin X$$

Summing the forces along the y-axis, $$O_y = N - W*\cos X$$

Solving for F in the first equality, $$F = (W*V^2)/(G*R) + W*\sin X$$

and, $$W = F/((V^2/(G*R)) + \sin X)$$

Solving for W in the second equality, $$W = N/\cos X$$

Equating the last two equations, $$F/((V^2/(G*R))+\sin X) = N/\cos X$$

Since $F = u*N$, $$(u*N)/((V^2/(G*R))+\sin X) = N/\cos X$$

and, $$u*\cos X = V^2/(G*R) + \sin X$$

Solving for V, $$V1_s = [G*R*(u\cos X - \sin X)]^{\frac{1}{2}}$$

With respect to FIGS. 2b and 2c, it can be mathematically shown that for the velocity at which vehicle 12 will begin to slide in this cornering situation is:

$$V2_s = [G*R*(u\cos X - \sin X)/(\cos X + u*\sin X)]^{\frac{1}{2}}$$

and that for the cornering situation shown in FIGS. 3b and 3c, $$V3_s = [G*R((\tan X + u)/(1 - u*\tan X))]^{\frac{1}{2}}$$

Finally, it is also important to know the coefficient of friction u at which a vehicle begins to tip and slide at the same time for each of the three situations. This can be done by equating $V1_t$ and $V1_s$, $V2_t$ and $V2_s$, and $V3_t$ and $V3_s$ respectively. In each instance, it can be shown that for $$V1_t = V1_s, V2_t = V2_s, \text{ and } V3_t = V3_s$$

$$u = L/H$$

Figure 5:
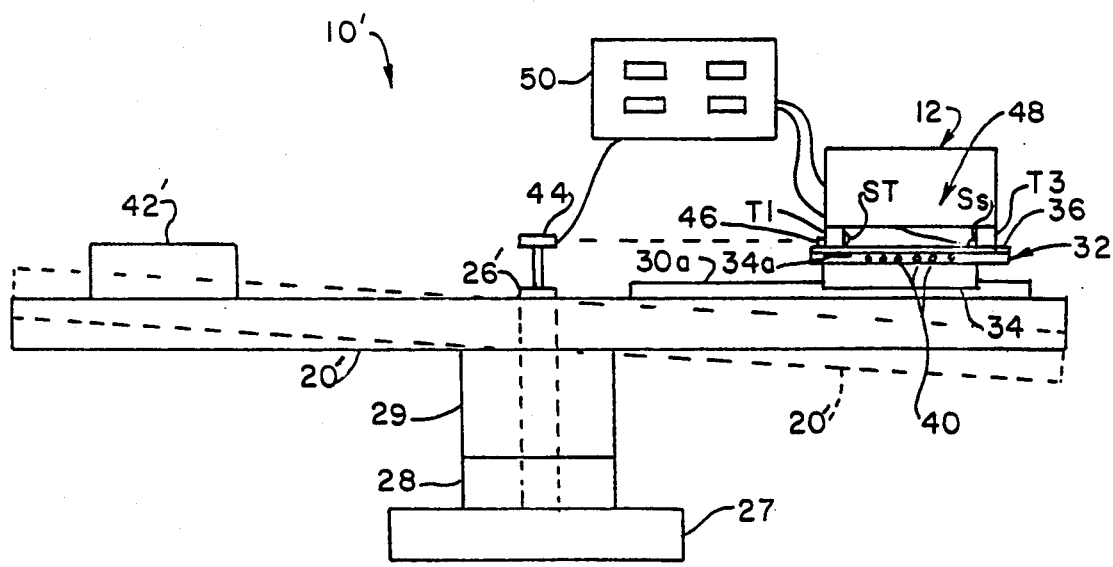
FIG. 5 is a side elevational view of a more complex apparatus for testing the cornering ability of a vehicle.

With respect to apparatus 10', as shown in FIGS. 5 and 6, it first includes a platform 20, which is shown to be of an elongate, rectangular shape but which can be any convenient size and shape. The platform has a longitudinal axis 22 and an orthogonal axis 24. Platform 20' is rotatable about its vertical axis and for this purpose a drive shaft 26' extends vertically upward through the center of the platform. The lower end of the shaft is fitted into a pedestal 27 or other convenient support. Platform 20' is rotatable through a wide range of speeds up to and including those speeds at which the vehicle may begin to tip over or slide. For this purpose, a turning mechanism 28 is connected to shaft 26' to turn the shaft and produce platform rotation. The platform is also tiltable about its vertical axis by a mechanism 29 which cants the platform with respect to shaft 26'. Tilting of the platform is important because it helps determine the vehicle's velocity at which sliding breakaway occurs for different slopes. A pair of rails 30a, 30b are set atop the platform. The rails are arranged parallel to each other and to the longitudinal axis 22 of the platform. The rails are equidistantly spaced on opposite side of axis 22. It is important to understand that a vehicle will either tip or slide depending upon its design. If it slides, for example, it will slide regardless of the slope of the turn. Therefore by tilting the platform to different angles, the speed at which sliding occurs for that road slope can be ascertained.

Slidably mounted atop the rails is a second platform 2. This second platform has guides 34 depending beneath its underside and attaching the platform to the rails for the platform to move back and forth along them. Platform 32 is smaller in size than platform 20', but the size of the platform is sufficiently large for vehicle 12 to rest upon it. The platform is mounted on the rails such that its longitudinal centerline overlays longitudinal axis 22 of platform 20'. The platform is rotatable about its own vertical axis to aid in aligning the axis of the vehicle's aft wheels and vertical axis 26. Fitted into the top of the platform are a pair of weighing scales 34a, 34b. These scales are located toward the inner end of platform 32 and are equidistantly spaced on opposite sides of the longitudinal centerline of the platform. As seen in FIG. 5, when vehicle 12 is in place atop platform 32, inner tires T1 and T2 respectively sit over weighing scales 34a, 34b. Platform 32 and scales 34a, 34b have a removable upper layer 36. The composition of this layer varies depending upon the type of road surface with which the vehicle is to be tested. Thus, layer 36 may be asphalt, concrete, dirt, or water. Further, nozzles 38 may be positioned adjacent the platform to spray water on the surface layer to wetten it; or, pipes 40 installed within platform 32 allows freon or another appropriate coolant to be piped beneath the surface to freeze the water into ice. Thus, rainy or icy road conditions can be simulated.

A counterweight 42' is placed on the end of platform 20' opposite from vehicle 12. The weight of the counterweight can vary depending upon the weight of the vehicle mounted on platform 32. Further, additional weight may be placed throughout platform 20' to produce dynamic balance of the platform. The amount of ballast is dependent upon the tilt of the platform, as well as the vehicle weight, so the ballast and counterweight provide the dynamic balance.

To properly orient the vehicle on platform 32, a theodolite 44 is used. The theodolite is positioned atop shaft 26'. An optical mirror 46 is mounted on the outside of vehicle 12, i.e. on the outside of tire T1 to facilitate platform 32 and vehicle 12 alignment. The mirror provides a line-of-sight which should be parallel to the axis of the aft wheels. The mirror may have a cross-hairs formed on its outer face with the center of the cross-hairs aligned with the aft wheels, axis. The distance $R_T$ to the fixture is measured from the axis 26 of platform rotation to tire T1, and is the turn radius of the vehicle. The smallest turn radius for the vehicle can be found by driving the vehicle in small, tight circles and measuring the radius $R_T$ of the turn. In establishing this distance, vehicle 12 is first set upon surface 36 of the platform. Next, the vehicle or platform 32 is rotated until the centerline of the vehicle's aft wheel axle is in line with the axis of the theodolite. Platform 32 is then moved back and forth along the rails until the measured distance between axis 26' and tire T1 equals $R_T$, and the mirror and theodolite are aligned. Also, the vehicle's steering wheel is turned to one "lock" position (maximum turn angle) to simulate turning in a tight turn. Then, the platform is locked in position so it can no longer move over the rails. This fixed platform position is maintained throughout the test. In testing for vehicle stability, the platform does not have to be tilted. This is because if the vehicle starts to roll over before it slides on level ground, it will also start to do so on any slope (the difference being the speed at which this will occur). Lastly, a chain (not shown) can be used to chain the vehicle to the platform.

Next, apparatus 10 includes a sensor means indicated generally 48 for determining when vehicle 12 begins to slide or tip over. Weighing scales 34a, 34b will sense when the wheels lift off the platform; i.e., vehicle 12 begins to tip over. Next, sensor means 48 includes a sensor $S_s$ attached at each outer wheel of the vehicle for sensing when the vehicle overcomes friction and begins to slide laterally. These sensors are attached to the inside of respective outer tires T3 and T4. The respective sensors are connected to a monitor 50, as are the scales 34a, 34b. The monitor is also capable of recording vehicle velocity as well as the weight impressed on each scale at any one time.

In use, the appropriate surface layer 36 is installed on platform. Next, the vehicle, with sensors mounted on the tires, is placed on the platform with the inner tires T1 and T2 set over scales 34a, 34b. Mechanism 29 is used to tilt platform 20' until the angle X (the angle of incline of the roadway 18 to the horizontal) is reached. Thus, the various conditions for which the above calculations were made are simulated. For testing purposes, two types of tilting mechanisms will be employed. For testing a vehicle turning on a banked curve or going around a hill, the platform 32's axis of rotation is vertical while that of platform 20 is inclined to the vertical. When testing for a vehicle turning uphill on an incline, platform 32's axis will be inclined as well as that of platform 20.

During the test, as the various calculated velocities for vehicle 12 are reached, monitor 50 records whether the vehicle begins to tip, to slide, or both. If the vehicle begins to tip, this will be noted by a diminution of the weight recorded on scales 34a, 34b, for when the vehicle starts to tip over, it is the inner wheels which first lift off the surface. If the vehicle begins to slide, this lateral movement will be sensed by sensors $S_s$.

Referring to FIGS. 7a-7f, various types of suspensions 14 for vehicle 12 are shown. These various suspensions are well-known in the art and will not be described in detail. It will be understood that for different vehicle designs, such factors as the vehicles center of gravity, wheel spacing, etc. may mitigate in favor of use of a particular one of these suspension systems. Regardless of the suspension used, testing apparatus 10 can be used to determine if the vehicle with such suspension is safe for use under the variously discussed cornering conditions set forth hereinabove. With respect to an analysis of suspension systems and factors to be considered in their design and use, see my paper titled VEHICLE CORNERING STABILITY AND CG LIMITS which was presented to the Society of Allied Weight Engineers, Inc. (SAWE) at their annual conference held May 21-23, 1990.

One of the applications of apparatus 10 is to determine whether a vehicle 12's design is such that the vehicle will be stable in turning situations; i.e. it will not tip over. To accomplish this, is, in effect, to determine the upper, vertical center of gravity limit of the vehicle. As previously indicated, if a vehicle looses traction in a turn so that it slides or skids, the driver still has a chance to take corrective action and bring the vehicle back under full control. If a vehicle starts to tip over, the driver's chances of regaining control are much less likely. For any of the suspension systems shown in FIGS. 7a-7f, when vehicle 12 is making a sharp turn, just before tipping over, the inside wheels T1, T2 of the vehicle start to raise off the ground. The inner components of the suspension will be fully extended at that point, and the outer components fully compressed.

Referring to FIGS. 8-15, a twin control arm or wishbone suspension system, see FIG. 7B, is represented for a vehicle in a turning situation such as described above. In addition to the symbols previously defined, the following symbols indicate the following:

$B_F$ = The forward suspension's horizontal distance from the center of the outer wheel to the projected center line of the vehicle on the ground when the vehicle is inclined during the turning maneuver, just before tipping. (See FIG. 8)

$B_A$ = The rear suspension's horizontal distance from the center of the outer wheel to the projected center line of the vehicle on the ground when the vehicle is inclined during the turning maneuver, just before tipping. (See FIG. 9)

S = The horizontal distance from the forward axle to the rear axle (i.e., the wheel base of the vehicle), x = The horizontal distance from the forward axle to the vehicle's center of gravity.

Y = The maximum expected horizontal lateral distance from the vehicle's center line to the center of gravity.

$b_{CG}$ = The angle between the road and the vehicle center line the instant the second wheel clears the road ($b_A$ or $b_F$ whichever is the largest of the two). (See FIGS. 8-10))

$CL_A$ = The distance (along the vehicle's center line) from the ground to the reference water line (the instant the second wheel clears the ground) of the rear suspension. (See FIG. 9)

$CL_F$ = The distance (along the vehicle's center line) from the ground to the reference water line (the instant the second wheel clears the ground) of the forward suspension. (See FIG. 10)

WL = The reference (water line) of the vehicle.

Figure 8:
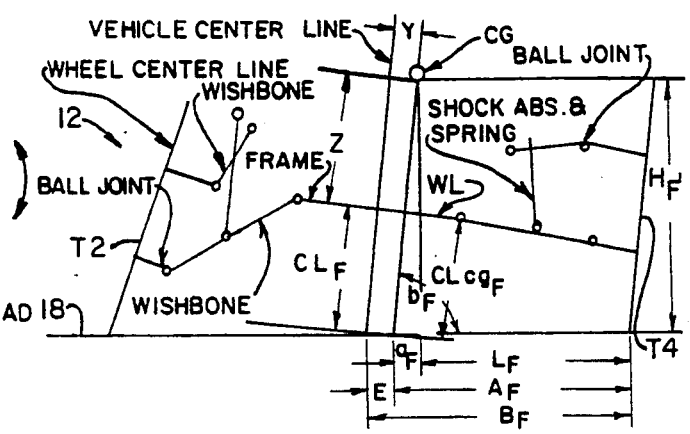
Figure 9:
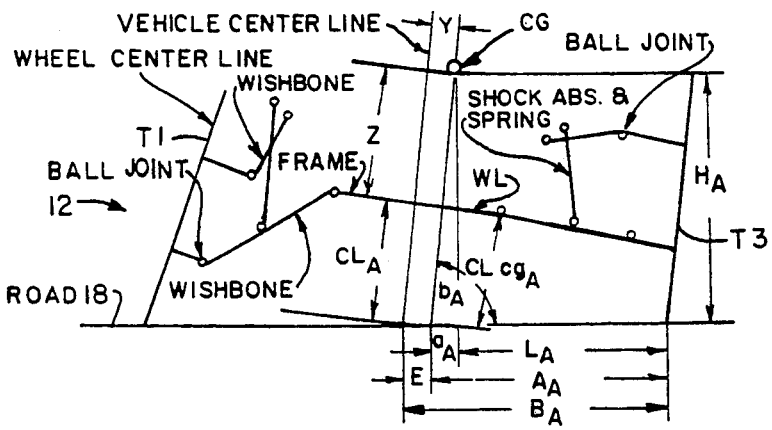

With respect to FIG. 8, the forward portion of the suspension is represented for a vehicle 12 leaning into a turn. For this situation, it is assumed that the vehicle weight is on the outer two wheels. It is also assumed that the suspension spring rate is either known or can be measured. As shown, the forward suspension is extended as far as possible with respect to inner wheel T1; while the other side of the suspension is in compression for outer wheel T3. FIG. 9 illustrates the rear portion of the suspension system in which the suspension is extended as far as possible with respect to inner wheel T1 and in compression with respect to outer wheel T3. With respect to FIG. 8, values for Y, $CL_F$, $A_F$, $B_F$, $CL_{cgF}$, and $b_F$ can be obtained. With respect to FIG. 9, values for Y, $CL_A$, $A_A$, $B_A CL_{cgA}$, and $b_A$ can be obtained. Since, in a sharp turn, one of the inner wheels will typically leave the ground before the other, it is important to determine the relation between the center of gravity and the outer wheels at the instant the second inner wheel leaves the ground. This is done by comparing $F_F$ and $B_A$, selecting the larger value of the two and rotating the vehicle's axle associated with that portion of the suspension through the smallest angle necessary to have the angle between the vehicle's center line and the road be the same for both axles.

Figure 10:
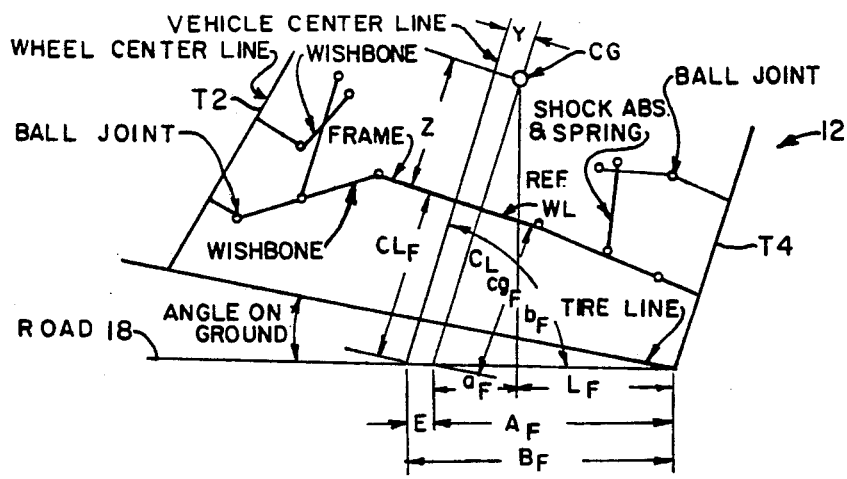
Figure 11:
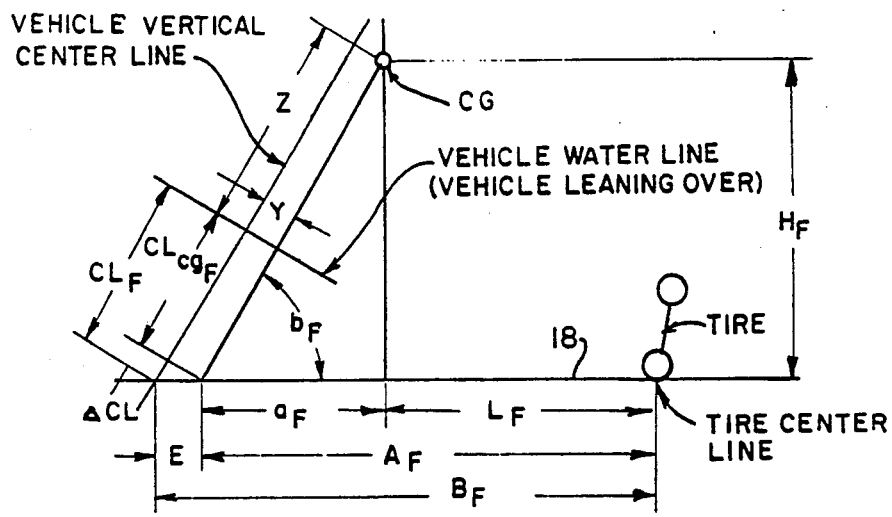
Figure 12:
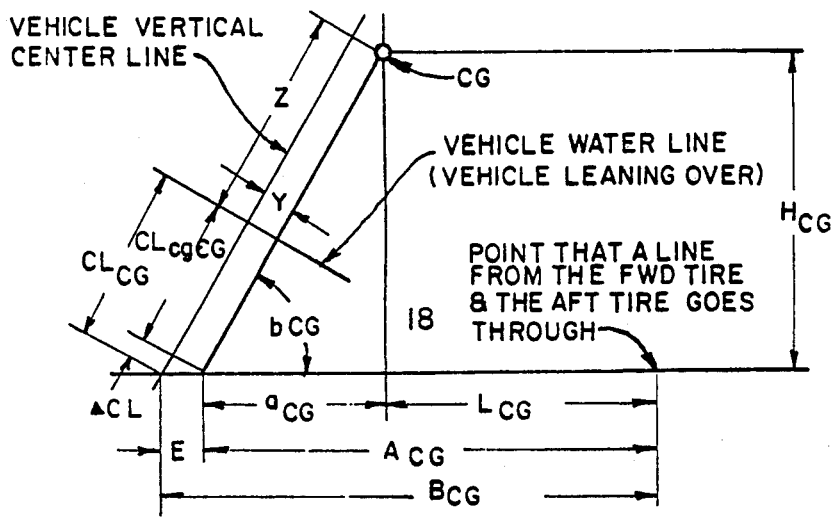
Figure 13:
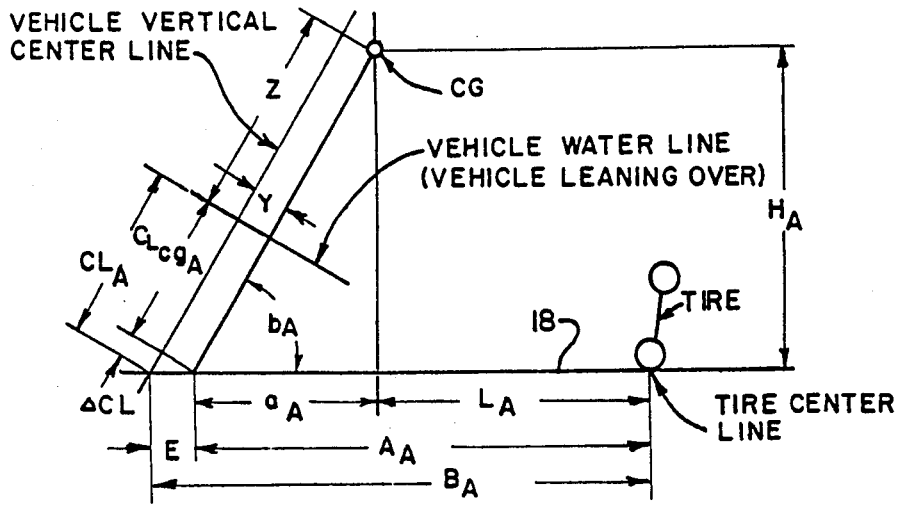
Figure 14:
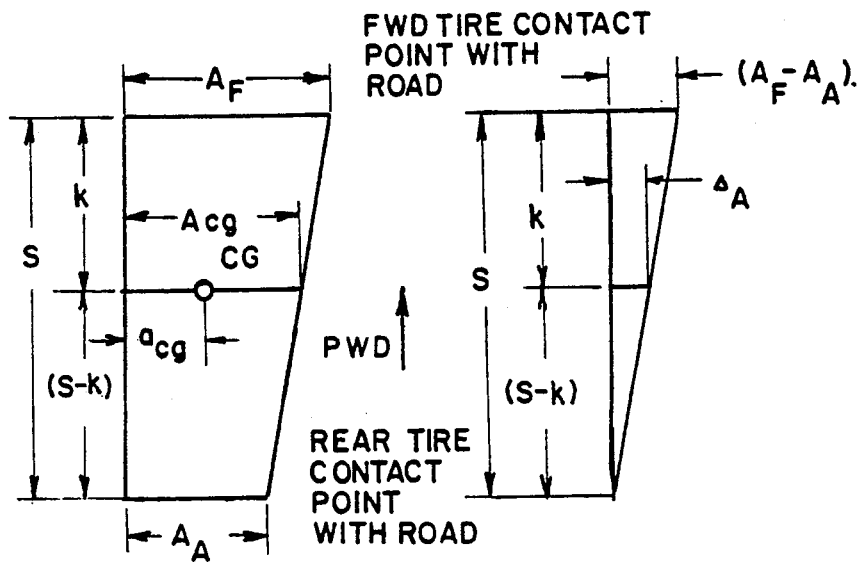
FIG. 14 is a view looking down toward the road.
Figure 15:
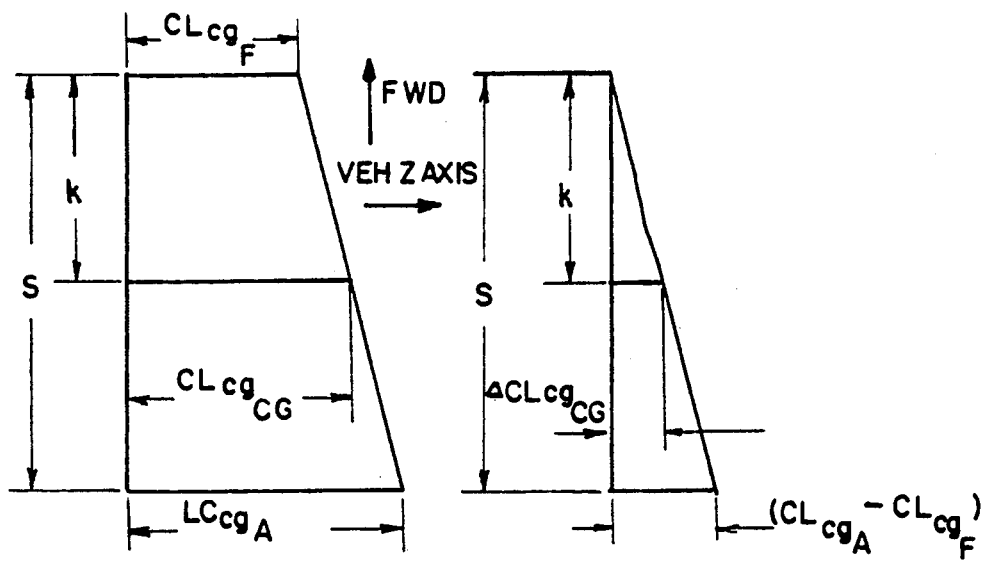
FIG. 15 is a view looking perpendicular to the side of the vehicle.

FIG. 10 illustrates the forward portion of the suspension system with tire T2 lifted off the ground, this being the instant before rear inner tire T1 clears the ground. FIGS. 11-13 represent respective simplified geometric lateral relationships between the suspension and vehicle 12's center of gravity. FIG. 11 is with respect to the forward portion of the suspension, FIG. 12 at a point corresponding to the location of the vehicle's center of gravity, and FIG. 13 at the rear portion of the suspension. FIGS. 14 and 15 are, respectively, a view looking down from the top of vehicle 12 to the road, and a view looking perpendicular to the side of the vehicle. With respect to these two latter figures, by knowing the longitudinal distance k from the forward axle to the vehicle's center of gravity, the wheel base S of the vehicle, and the coefficient of friction u between the tires and road, the maximum vertical distance Z from the vehicle's frame to the center of gravity can be derived as follows:

With respect to FIG. 11, $$\text{Tan } b_F = \frac{H_F}{a_F}$$

Similarly, with respect to FIGS. 12 and 12, $$\text{Tan } b_{CG} = \frac{H_{CG}}{a_{CG}},$$

and $$\text{Tan } b_A = \frac{H_A}{a_A}.$$

With respect to FIG. 14, $$\frac{dA}{S-k} = \frac{A_F - A_A}{S}$$

or, $$dA = \frac{(A_F - A_A)(S - k)}{S}$$

Since, $$A_{CG} = A_A + dA.$$

$$A_{CG} = A_A + \left[ \frac{(A_F - A_A)(S - K)}{S} \right]$$

With respect to FIG. 15, $$\frac{dCL_{cgCG}}{k} = \frac{(CL_{cgA} - CL_{cgF})}{S},$$

or, $$dCL_{cgCG} = \frac{(k)(CL_{cgA} - CL_{cgF})}{S}.$$

Since, $$CL_{cgCG} = CL_{cgF} + dCL_{cgCG},$$

then, $$CL_{cgCG} = CL_{cgF} + \frac{(k)(CL_{cgA} - CL_{cgF})}{S}$$

With respect to FIG. 12, $$a_{CG} = A_{CG} - L_{CG}.$$

As previously shown, $$u = \frac{L_{CG}}{H_{CG}},$$

or, $$L_{CG} = (u)(H_{CG}).$$

From the foregoing relationships, $$a_{CG} = \frac{H_{CG}}{\text{TAN } b_{CG}},$$

or, $$\frac{H_{CG}}{\text{Tan } b_{CG}} = A_{CG} - L_{CG}.$$

Further combining, $$\frac{H_{CG}}{\text{Tan } b_{CG}} = A_{CG} - ((u)(H_{CG})).$$

$$\frac{H_{CG}}{\text{Tan } b_{CG}} + ((u)(H_{CG})) = A_{CG},$$

$$(H_{CG}) \left[ \frac{1}{\text{Tan } b_{CG}} + u \right] = A_{CG},$$

$$H_{CG} = \frac{A_{CG}}{\left[ \frac{1}{\text{Tan } b_{CG}} + u \right]}$$

Referring again to FIG. 12, $$\text{Sin } b_{CG} = \frac{H_{CG}}{Z + CL_{cgCG}},$$

or, $$(Z)(\text{Sin } b_{CG}) + (CL_{cgCG})(\text{Sin } b_{CG}) = H_{CG},$$

and, $$Z = \frac{H_{CG} - (CL_{cgCG}(\text{Sin } b_{CG}))}{\text{Sin } b_{CG}}.$$

Further combining, $$Z = \frac{\dfrac{A_{CG}}{\left[ \dfrac{1}{\text{Tan } b_{CG}} + u \right]} - \left[ CL_{cgF} + \dfrac{(k)(CL_{cgA} - CL_{cgF})}{S} \right](\text{Sin } b_{CG})}{\text{Sin } b_{CG}}$$

which can also be expressed as $$\frac{\left[\frac{(A_F - A_A)(S - k)}{S} + A_A\right]}{\left[\frac{1}{\text{Tan } b_{CG}} + u\right]} - \left[CL_{cgF} + \frac{(k)(CL_{cgA} - CL_{cgF})}{S}\right](\text{Sin } b_{CG})$$

which reduces to $$A_A = B_A = E.$$

$$\left\{\frac{\left[\frac{(A_F - A_A)(S - k)}{S} + A_A\right]}{\left[\frac{1}{\text{Tan } b_{CG}} + u\right](\text{Sin } b_{CG})}\right\} - \left[CL_{cgF} + \frac{(k)(CL_{cgA} - CL_{cgF})}{S}\right]$$

Since, $$\text{Tan } b_{CG} = \frac{Y}{CL},$$

$$dCL = \frac{Y}{\text{Tan } b_{CG}}.$$

Referring to FIG. 13, $$CL_A = CL_{cgA} + dCL,$$

or, $$CL_{cgA} = CL_A - dCL.$$

And, $$CL_{cgA} = CL_A - \frac{Y}{\text{Tan } b_{CG}}.$$

It will be understood that a similar equation can be derived for the forward suspension equation of the vehicle, so that:

$$CL_{cgF} = CL_F - \frac{Y}{\text{Tan } b_{CG}}.$$

Again referring to FIG. 12, $$\text{Sin } b_{CG} = \frac{Y}{E}$$

or, $$E = \frac{Y}{\text{Sin } b_{CG}}.$$

Referring to FIG. 13,

Referring to FIG. 11, $$A_F = B_F - E.$$

Substituting for E in the two preceding equations, $$A_A = B_A - \frac{Y}{\text{Sin } b_{CG}}$$

and, $$A_F = B_F - \frac{Y}{\text{Sin } b_{CG}}$$

Substituting for $A_A$ and $A_F$ in the previous equation solved for Z, $$Z = \frac{\left\{\frac{\left[\left(B_F - \frac{Y}{\text{Sin } b_{CG}}\right) - \left(B_A - \frac{Y}{\text{Sin } b_{CG}}\right)\right](S - k)}{S} + \left(B_A - \frac{Y}{\text{Sin } b_{CG}}\right)\right\}}{\left[\frac{1}{\text{Tan } b_{CG}} + u\right](\text{Sin } b_{CG})} -$$

$$\left\{\frac{(k)\left[\left(CL_A - \frac{Y}{\text{Tan } b_{CG}}\right) - \left(CL_F - \frac{Y}{\text{Tan } b_{CG}}\right)\right]}{S} + \left[CL_F - \frac{Y}{\text{Tan } b_{CG}}\right]\right\}$$

This reduces to:

$$Z = \left\{\frac{\frac{[B_F - B_A](S - k)}{S} + B_A - \frac{Y}{\text{Sin } b_{cg}}}{\left[\frac{1}{\text{Tan } b} + u\right]\text{Sin } b_{cg}}\right\} -$$

$$\left\{\frac{(k)[CL_A - CL_F]}{S} + CL_F - \frac{Y}{\text{Tan } b_{cg}}\right\}$$

The above equation is used to calculate the maximum safe distance "Z" from the vehicle reference water line (see FIGS. 9 and 10) to the center of gravity of the vehicle. As used in the equation:

U = The coefficient of friction between the road and the tire on the surface the vehicle is going to be driven. Note: If the rear suspension clears the ground before the front suspension, FIG. 9 will look like FIG. 10 and vice versa.

In order to obtain the complete CG envelope, and to insure obtaining the safe CG limit, "Z" should be solved for the following conditions:
1) Empty vehicle weight.
2) Vehicle maximum gross weight.
3) Maximum forward CG condition based on probable vehicle loadings.
4) Maximum rear CG condition based on probable vehicle loadings.
5) Maximum lateral center of gravity offset based on probable vehicle loadings.

It will be appreciated that some vehicles like large trucks, will not meet the vertical CG requirement after loading. In such instances, the limits of certain equations must be calculated and the truck user advised of any turning limitations. Further, by knowing all the variables needed in the equation, it is possible to define a safe vehicle vertical CG limit. This will, in turn, help define vehicle loading and the establishment of a proper relationship between the vehicle's height and its wheel tread. This will be so even if the vehicle is a small truck, a tracked vehicles, or an off-road vehicle.

In view of the above, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. Apparatus for testing the cornering stability of a vehicle to determine when the vehicle begins to slide or tip over comprising:
    a movable platform capable of supporting the weight of a vehicle, the vehicle being positioned on one end of the platform with a longitudinal centerline of the vehicle being orthogonal to the longitudinal axis of the platform;
    a counterweight positioned at an opposite end of the platform from the vehicle;
    means for rotating the platform through a range of speeds to simulate vehicle movement in a circular path such as when the vehicle is rounding a corner; and,
    sensor means attached to the vehicle for detecting movement of the vehicle relative to the platform.

2. The apparatus of claim 1 wherein the vehicle is positioned on the platform with a centerline longitudinal axis of the vehicle orthogonal to a line extending radially outwardly from the center of the platform surface, the vehicle, when so positioned, having an inner set of wheels and an outer set of wheels with respect to a direction of rotation of the platform and the sensor means includes a sensor attached at each inner wheel of the vehicle for sensing when the wheel lifts off the platform.

3. The apparatus of claim 2 wherein the sensor means further includes a sensor attached at each outer wheel of the vehicle for sensing when the vehicle overcomes friction and begins to slide laterally.

4. The apparatus of claim 3 further include weighing means for weighing the vehicle as it rests upon the platform.

5. The apparatus of claim 4 wherein the weighing means further includes a pair of scales upon each of which respectively rests one wheel of the vehicle.

6. The apparatus of claim 1 further including means for tilting the platform to simulate movement of the vehicle around hills.

7. The apparatus of claim 6 wherein the tilting means includes means for tilting the platform to simulate movement of the vehicle turning uphill and on an incline.

8. The apparatus of claim 1 wherein the surface on which the vehicle rests is removable and a different surface can be substituted therefore, whereby the cornering ability of the vehicle on different surfaces can be tested.

9. The apparatus of claim 8 further including at least one rail upon which the removable surface is mounted.

10. The apparatus of claim 9 including a pair of rails set parallel to each other and to a centerline of the platform, whereby the vehicle can move radially outwardly with respect to the center of the platform to simulate turning of the vehicle through a curve.

11. The apparatus of claim 10 wherein the removable surface forms an upper portion of a second and smaller platform than the first said platform, said second platform having guide means depending therebeneath to slidably mount the second platform on the rails, and said vehicle being positioned on said second platform.

12. The apparatus of claim 11 wherein said second platform is rotatable for aligning the vehicle with said first platform.

13. The apparatus of claim 11 wherein the removable surface may be one a number of different surfaces over which the vehicle travels.

14. The apparatus of claim 13 further including means for wetting the removable surface to simulate rainy road conditions.

15. The apparatus of claim 14 further including means for freezing water on the removable surface to simulate icy road conditions.

16. The apparatus of claim 11 further including means for aligning the vehicle and second platform with respect to the first said platform to simulate various turn radii.

17. The apparatus of claim 16 wherein the alignment means includes a theodolite positioned relative to the axis of rotation of the first said platform, and an optical mirror mounted on the second platform.

18. The apparatus of claim 1 further including monitoring means to which the sensors are connected for recording an output from the sensors.

19. Apparatus for testing the cornering stability of a vehicle to determine when the vehicle begins to slide or tip over comprising:
    a movable platform capable of supporting the weight of a vehicle, the vehicle being positioned at one end of the platform;
    a counterweight positioned at an opposite end of the platform from the vehicle;
    means for rotating the platform through a range of speeds to simulate vehicle movement in a circular path such as when the vehicle is rounding a corner;

means for tilting the platform to simulate movement of the vehicle around hills and for tilting the platform to simulate movement of the vehicle turning uphill and on an incline; and, sensor means attached to the vehicle for detecting movement of the vehicle relative to the platform, the vehicle being positioned on the platform with a central longitudinal axis of the vehicle orthogonal to a line extending radially outwardly from the center of the platform surface, the vehicle, when so positioned, having an inner set of wheels and an outer set of wheels with respect to the direction of rotation of the platform, the sensor means including a sensor attached at each inner wheel of the vehicle for sensing when an inner wheel lifts off the platform, and further including a sensor attached at each outer wheel for sensing when the vehicle overcomes friction and begins to slide laterally.

* * * * *